(12) United States Patent
George et al.

(10) Patent No.: US 10,939,872 B2
(45) Date of Patent: Mar. 9, 2021

(54) PATIENT CARE DEVICES WITH NETWORK VARIABLES

(71) Applicant: Stryker Corporation, Kalamazoo, MI (US)

(72) Inventors: Christopher Alan George, St. Thomas (CA); Madhu Thomas, London (CA); Jonathan Mark Greenbank, Plainwell, MI (US); Sujay Sukumaran, Portage, MI (US); Marko N. Kostic, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 207 days.

(21) Appl. No.: 15/995,635

(22) Filed: Jun. 1, 2018

(65) Prior Publication Data

US 2018/0344254 A1    Dec. 6, 2018

Related U.S. Application Data

(60) Provisional application No. 62/513,636, filed on Jun. 1, 2017.

(51) Int. Cl.
*A61G 7/018* (2006.01)
*A61G 7/015* (2006.01)
(Continued)

(52) U.S. Cl.
CPC .......... *A61B 5/6891* (2013.01); *A61B 5/0015* (2013.01); *A61B 5/1115* (2013.01); *A61G 7/018* (2013.01); *A61G 7/0524* (2016.11); *A61G 7/0527* (2016.11); *G08B 21/0461* (2013.01); *G16H 40/63* (2018.01); *G16H 40/67* (2018.01);
(Continued)

(58) Field of Classification Search
None
See application file for complete search history.

(56) References Cited

U.S. PATENT DOCUMENTS

| | | | |
|---|---|---|---|
| 5,649,105 A | 7/1997 | Aldred et al. | |
| 6,920,485 B2 | 7/2005 | Russell | |

(Continued)

OTHER PUBLICATIONS

Wayback Machine capture of "C++ Class Access Modifiers", Oct. 6, 2011 (Year: 2011).*

(Continued)

*Primary Examiner* — Danny Chan
(74) *Attorney, Agent, or Firm* — Warner Norcross + Judd LLP

(57) ABSTRACT

A first node of a patient care device processes data relating to the patient care device and sets a public variable equal to a value of the data. A second node receives the public variable from the first node, sets a private variable equal to the value of the public variable, and executes a software program that reads the private variable but not the public variable. In other embodiments, the second node checks to see if the public variable is registered at the second node, and if so, uses the private variable in carrying out a function. The first node executes a first software program that sets the public variable to the value and relies on a service to share the value with the second node. The sharing occurs despite the first software program not containing any instructions for transmitting the value or variable to the second node.

12 Claims, 5 Drawing Sheets

(51) Int. Cl.
*A61G 7/012* (2006.01)
*A61G 7/05* (2006.01)
*A61B 5/00* (2006.01)
*A61B 5/11* (2006.01)
*G08B 21/04* (2006.01)
*G16H 40/63* (2018.01)
*G16H 40/67* (2018.01)

(52) U.S. Cl.
CPC .............. *A61G 7/012* (2013.01); *A61G 7/015* (2013.01); *A61G 7/0506* (2013.01); *A61G 7/0516* (2016.11)

(56) References Cited

U.S. PATENT DOCUMENTS

| | | |
|---|---|---|
| 6,939,080 B2 | 9/2005 | Wokas |
| 6,999,998 B2 | 2/2006 | Russell |
| 7,536,421 B2 | 5/2009 | Tsinman et al. |
| 7,598,853 B2 | 10/2009 | Becker et al. |
| 9,320,662 B2 | 4/2016 | Hayes et al. |
| 2004/0128673 A1* | 7/2004 | Fuchs .................... G06F 9/542 719/310 |
| 2005/0229321 A1* | 10/2005 | Phillips ................ A61G 7/0509 5/715 |
| 2008/0172789 A1 | 7/2008 | Elliot et al. |
| 2008/0189865 A1* | 8/2008 | Bhai .................. A61G 7/05769 5/706 |
| 2009/0169007 A1* | 7/2009 | Vasicheck ........... H04L 63/0428 380/255 |
| 2010/0333175 A1 | 12/2010 | Cox et al. |
| 2012/0117730 A1* | 5/2012 | Lemire .................... A61G 5/10 5/611 |
| 2015/0231006 A1 | 8/2015 | Bhimavarapu et al. |
| 2015/0290060 A9 | 10/2015 | Hayes |
| 2016/0158083 A1 | 6/2016 | Lambarth et al. |
| 2017/0098359 A1 | 4/2017 | Sidhu et al. |
| 2018/0153753 A1* | 6/2018 | Kostic .................. A61G 7/0527 |
| 2018/0295112 A1* | 10/2018 | Coppola ............. H04L 63/0457 |

OTHER PUBLICATIONS

Joerns Healthcare User-Service Manual Joems Bariatric Bed, Model Bari10A, 2010.
Stryker Operations Manual Epic II Critical Care Bed, Model 2030, Jan. 2010.
Stryker Bertec Operations Manual the GO Bed Electric Acute Care Bed, Dec. 2000.
Stryker Operations Manual InTouch Critical Care Bed Model FL27, Apr. 2012.
Stryker Patient Care Maintenance Manual Modular Patient System (MPS) 3000 Bed, Mar. 1994.
Stryker Medical Secure 3000 Bed Operations Manual.

* cited by examiner

PATIENT CARE DEVICES WITH NETWORK VARIABLES

CROSS-REFERENCE TO RELATED APPLICATIONS

This application claims priority to U.S. provisional patent application Ser. No. 62/513,636 filed Jun. 1, 2017, by inventors Christopher George et al. and entitled PATIENT CARE DEVICES WITH NETWORK VARIABLES, the complete disclosure of which is incorporated herein by reference.

BACKGROUND

The present disclosure relates to patient care devices, such as patient support apparatuses (e.g. beds, stretchers, chairs, recliners, operating tables, cots, etc.), thermal control units adapted to control a person's temperature, and other types of medical devices.

Some patient care devices include embedded systems having multiple nodes that communicate with each other. The nodes typically share information with each other by executing programs that include instructions for transferring data to other nodes, requesting data from other nodes, and/or otherwise processing data that is sent to, or originates from, other nodes. These inter-node communication instructions often need to be rewritten anytime a change is made to the design of the patient care device that involves the addition of a new node, a removal of a node, a consolidation of two or more nodes, a different communication medium, a new desired recipient of particular data, a new source of particular data, new or revised software executed by a node, and/or other changes to the nodes and the data communicated therebetween. Updates and/or changes to the patient care device can therefore be difficult.

SUMMARY

Patient care devices according to one or more aspects of the present disclosure include embedded communication systems that provide greater flexibility for changes and redesigns. The embedded communication system utilizes network variables that are managed in the background by services running on the nodes. The network variables are updated and shared by the services in a manner that is transparent to the mainline applications executing on the nodes. Data resident on another node that is to be utilized by a mainline application on another node therefore appears to be local to the mainline application, and the mainline application need not include instructions for retrieving the desired data and/or keeping track of where the desired data resides. Local mainline applications are therefore able to treat data resident on different nodes, or data that is to be delivered to different nodes, as if the data were purely local, thereby avoiding the need for changes to be made to the local mainline applications if the sources and/or recipients of the data change, or if other aspects of the network change, such as, but not limited to, one or more of the lower layers of the communication network (e.g. physical layer, data link layer, etc.)

According to a first embodiment of the present disclosure, a patient support apparatus is provided having a support surface for a person, a first node, and a second node. The first node includes a first controller adapted to process data relating to the patient support apparatus and to set a first public variable equal to a first value of the data. The second node includes a second controller adapted to receive the first public variable from the first node via a communication medium, set a first private variable equal to the first value of the first public variable, and execute a software program that reads the first private variable but not the first public variable.

According to other aspects of the present disclosure, the second controller interrupts execution of the software program to set the first private variable equal to the first value, and the software program does not include instructions for retrieving the first public variable from the first node.

The first controller may further be adapted to update the first public variable to a second value of the data, and the second controller may further be adapted to set the first private variable equal to the second value of the first public variable.

In some embodiments, a third node having a third controller is included. The third controller is adapted to receive the first public variable from the first controller via the communication medium. The third controller may further be adapted to set a second private variable equal to the first value of the first public variable, and execute a second software program that reads the second private variable but not the first public variable. Alternatively, or additionally, the third node may process second data relating to the patient support apparatus which the third controller uses to set the first public variable equal to a second value of the second data, and to transmit the first public variable to the first and second nodes. In some embodiments, the third controller is programmed to not use the first public variable.

The second node may utilize a service that sets the first private variable equal to the first value of the first public variable.

In some embodiments, the first node controls a motor adapted to move a component of the patient support apparatus, and the first public variable relates to the component. Alternatively, the first node may control other aspects of the patient support apparatus, including, but not limited to, an exit detection system, a propulsion system, a user interface, an off-board communication link, and one or more force sensors adapted to detect a weight of a patient positioned on the support surface.

According to another embodiment of the present disclosure, a patient support apparatus is provided that includes a patient support surface, a first node, a first software program, a second node, and a first service. The first node includes a first controller adapted to process data relating to the patient support apparatus. The first software program is executed by the first controller and causes the first controller to set a first variable equal to a first value of the data. The second node includes a second controller adapted to execute a second software program that utilizes the first value of the data. The first service is also executed by the first controller and shares the first value with the second node via a communication medium. The first software program does not contain any instructions for transmitting the first variable to the second node.

According to other aspects of the present disclosure, the first service shares the first value with the second node by transmitting a public variable set equal to the first value of the first variable over the communication medium from the first node to the second node.

In some embodiments, a second service is executed by the second controller and sets a private variable at the second node equal to the first value of the public variable. The second software program reads the private variable at the second node but not the public variable.

The first service, in some embodiments, shares the first value with the second node by transmitting a message to the second node that also includes a timestamp indicating a time associated with the first value.

The service may share the first value with the second node by including the first value within a Binary Large OBject (BLOB) transmitted to the second node.

According to another aspect, a third node is also included that has a third controller. The first service shares the first value with the second node by broadcasting the first value to both the second and third nodes.

The first and second software programs may be independent of a data link layer and a physical layer of a communications protocol used to transmit the public variable over the communication medium.

The first variable is used in some embodiments to define a synchronization time at which the second and third nodes commence a synchronized activity.

According to still another aspect of the present disclosure, a patient support apparatus is provided having a patient support surface, a first node, a first service, and a second node. The first node includes a first controller that executes a first software program. The first software program processes data relating to the patient support apparatus and sets a first private variable equal to a first value of the data. The first service is executed by the first controller and sets a first public variable equal to the first value and transmits the first public variable over a communication medium. The second node has a second controller that is adapted to receive the first public variable from the first node via the communication medium, check to see if the first public variable is registered at the second node, and if the first public variable is registered, use the first value of the first public variable in carrying out at least one function.

In some embodiments, the second node includes a second software program and a second service, and the second service checks to see if the first public variable is registered at the second node. The second service sets a second private variable equal to the first value of the first public variable if the first public variable is registered at the second node. The second software program reads the second private variable but not the first public variable.

In any of the embodiments disclosed herein, the patient support apparatus may further include a plurality of siderails, a lift system adapted to raise and lower the support surface, and a plurality of wheels adapted to allow the patient support apparatus to be wheeled to different locations, as well as other components.

Before the embodiments of the disclosure are explained in detail, it is to be understood that the disclosure is not limited to the details of operation or to the details of construction and the arrangement of the components set forth in the following description or illustrated in the drawings. The disclosure may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the disclosure to any specific order or number of components. Nor should the use of enumeration be construed as excluding from the scope of the disclosure any additional steps or components that might be combined with or into the enumerated steps or components.

DETAILED DESCRIPTION OF THE EMBODIMENTS

Figure 1:
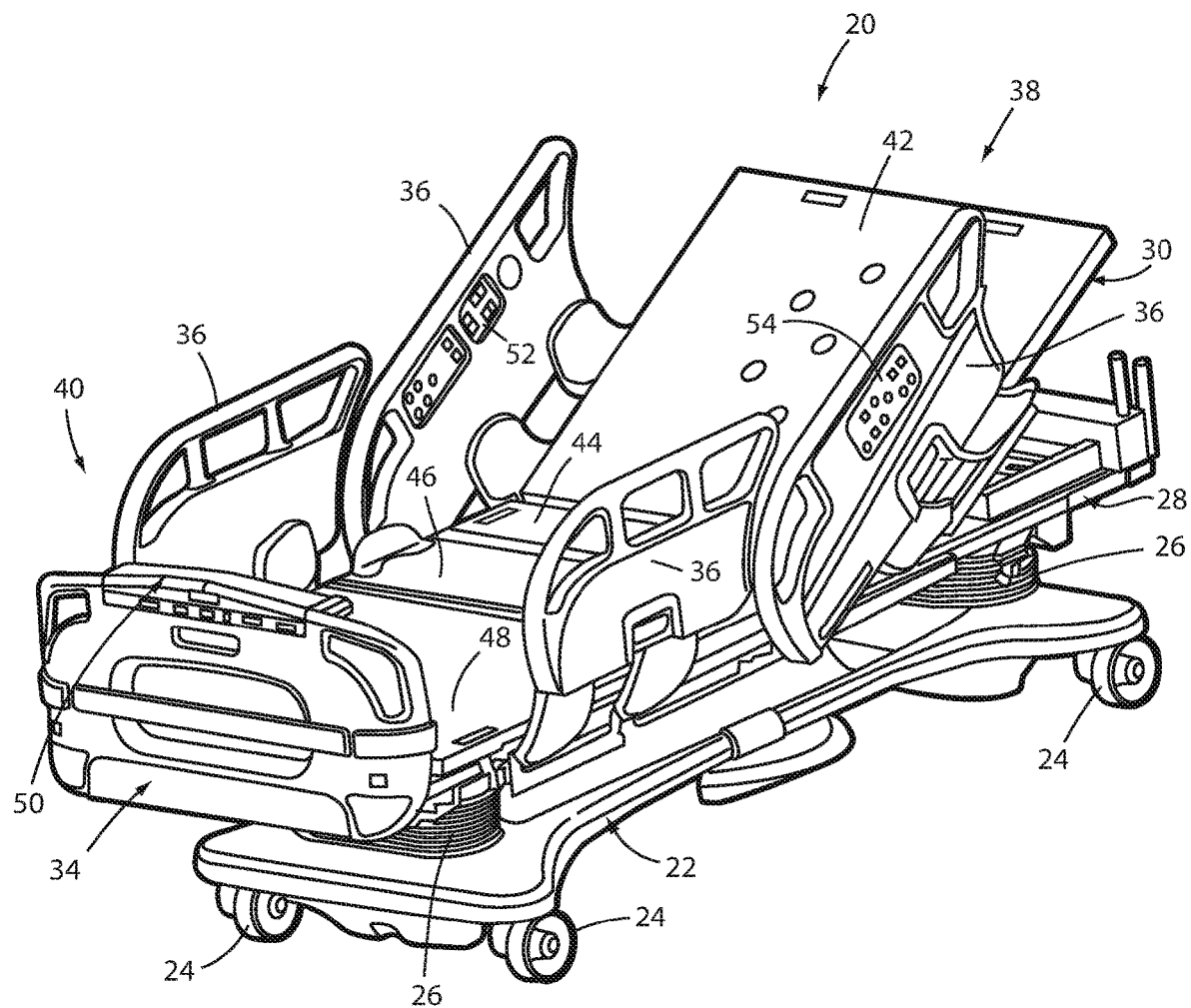
FIG. 1 is a perspective view of one example of a patient support apparatus according to one embodiment of the present disclosure.

FIG. 1 illustrates a patient support apparatus 20 that includes an improved communications system according to one embodiment. Although the particular form of patient support apparatus 20 illustrated in FIG. 1 is a bed adapted for use in a hospital or other medical setting, it will be understood that patient support apparatus 20 could, in different embodiments, be a cot, a stretcher, a gurney, a recliner, an operating table, or any other structure capable of supporting a person, whether stationary or mobile. It will also be understood that the communication system features of patient support apparatus 20 may be incorporated into other types of patient care devices, such as, but not limited to, thermal control systems used to control the temperature of a patient. Still other forms of patient support apparatuses and/or patient care device can incorporate the communication features described herein.

In general, patient support apparatus 20 includes a base 22 having a plurality of wheels 24, a pair of lifts 26 supported on the base, a litter frame 28 supported on the lifts 26, and a support deck 30 supported on the litter frame 28. Patient support apparatus 20 further includes a headboard (not shown), a footboard 34, and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, pneumatic actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard, footboard 34, and siderails 36. Support deck 30 provides a support surface for a mattress (not shown in FIG. 1), such as, but not limited to, an air, fluid, or gel mattress. Alternatively, another type of soft cushion may be supported on support deck 30 so that a person may comfortably lie and/or sit thereon. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Litter frame 28 is supported by two lift header assemblies (not shown) positioned on top of lifts 26. Each lift header assembly includes a pair of force sensors, which may be load cells, or other types of force sensors, such as, but not limited to, linear variable displacement transducers and/or any one or more capacitive, inductive, and/or resistive transducers that are configured to produce a changing output in response to changes in the force exerted against them. The force sensors are adapted to detect the weight of not only those components of patient support apparatus 20 that are supported by litter frame 28 (including litter frame 28 itself), but also any objects or persons who are wholly or partially being supported by support deck 30. As will be discussed in greater detail below, these force sensors may be part of an exit detection system and/or a scale system of patient support apparatus 20.

Any aspects of the physical construction of any of base 22, lifts 26, frame 28, deck 30, footboard 34, and siderails 36 that are not explicitly described herein may be constructed in the same manner as disclosed in commonly assigned, U.S. Pat. No. 7,690,059 issued to Lemire et al., and entitled HOSPITAL BED, the complete disclosure of which is incorporated herein by reference; or as disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference; or as embodied in the commercially available S3 bed sold by Stryker Corporation of Kalamazoo, Mich., and documented in the Stryker Maintenance Manual for Stryker's MedSurg Bed, Model 3002 S3, (doc. 3006-109-002 Rev D), published in 2010, the complete disclosure of which is also hereby incorporated herein by reference. The construction of any aspects of base 22, lifts 26, frame 28, deck 30, footboard 34 and/or siderails 36 that are not explicitly described herein may also take on other forms different from what is disclosed in these documents.

When patient support apparatus 20 is implemented as a stretcher or cot, any of its physical components not otherwise described herein may be constructed in any of the manners disclosed in commonly assigned U.S. Pat. No. 8,051,511 issued to Nahavandi et al. on Nov. 8, 2011 and entitled EMERGENCY STRETCHER; or commonly assigned U.S. Pat. No. 5,537,700 issued to Way et al. on Jul. 23, 1996 and entitled EMERGENCY STRETCHER WITH X-FRAME SUPPORT, the complete disclosures of both of which are hereby incorporated by reference herein. When patient support apparatus 20 is implemented as a recliner, those components of its physical construction not described herein may be the same as disclosed in commonly assigned U.S. patent application Ser. No. 14/212,253 filed Mar. 14, 2014 by inventors Christopher Hough et al. and entitled MEDICAL SUPPORT APPARATUS, the complete disclosure of which is also incorporated herein by reference. Still other physical constructions of patient support apparatuses 20 may be used when one or more of the patient support apparatuses 20 are implemented as cots, stretchers, and/or recliners.

Patient support apparatus 20 further includes a user interface 50 that enables a user of patient support apparatus 20 to control one or more aspects of patient support apparatus 20. Such aspects include, but are not limited to, changing a height of support deck 30, raising or lowering head section 42, activating and deactivating a brake for wheels 24, arming and disarming an exit detection system, and others. User interface 50 is implemented in the embodiment shown in FIG. 1 as a control panel having a lid (flipped down in FIG. 1) underneath which is positioned a plurality of controls. The controls may be implemented as buttons, dials, switches, or other devices. User interface 50 may also include a display for displaying information regarding patient support apparatus 20. The display is a touchscreen in some embodiments. Although FIG. 1 illustrates user interface 50 mounted to footboard 34, it will be understood that user interface 50 can be positioned elsewhere.

Patient support apparatus 20 also includes a pair of occupant user interfaces 52 and a pair of caregiver user interfaces 54 (only one of each of these is visible FIG. 1). Occupant user interfaces 52 are positioned on an inside surface of one or both of the head end siderails 36. Caregiver user interfaces 54 are positioned on an outside surface of one or both of the head end siderails 36. Occupant user interfaces 52 include controls intended to be used by an occupant, such as, but not limited to, controls for the up/down movement of litter frame 28, the pivoting of various of the deck sections, communication with a remotely positioned nurse, and one or more environmental features (e.g. volume and/or channel of a nearby television, etc.). Caregiver user interfaces 54 include controls intended to be used by a caregiver associated with the occupant of patient support apparatus 20, such as, but not limited to, controls for a brake of patient support apparatus 20, the exit detection subsystem incorporated into patient support apparatus 20, one or more lockouts that lock out selected controls of occupant user interfaces 52, and/or other features and functions of patient support apparatus 20.

Figure 2:
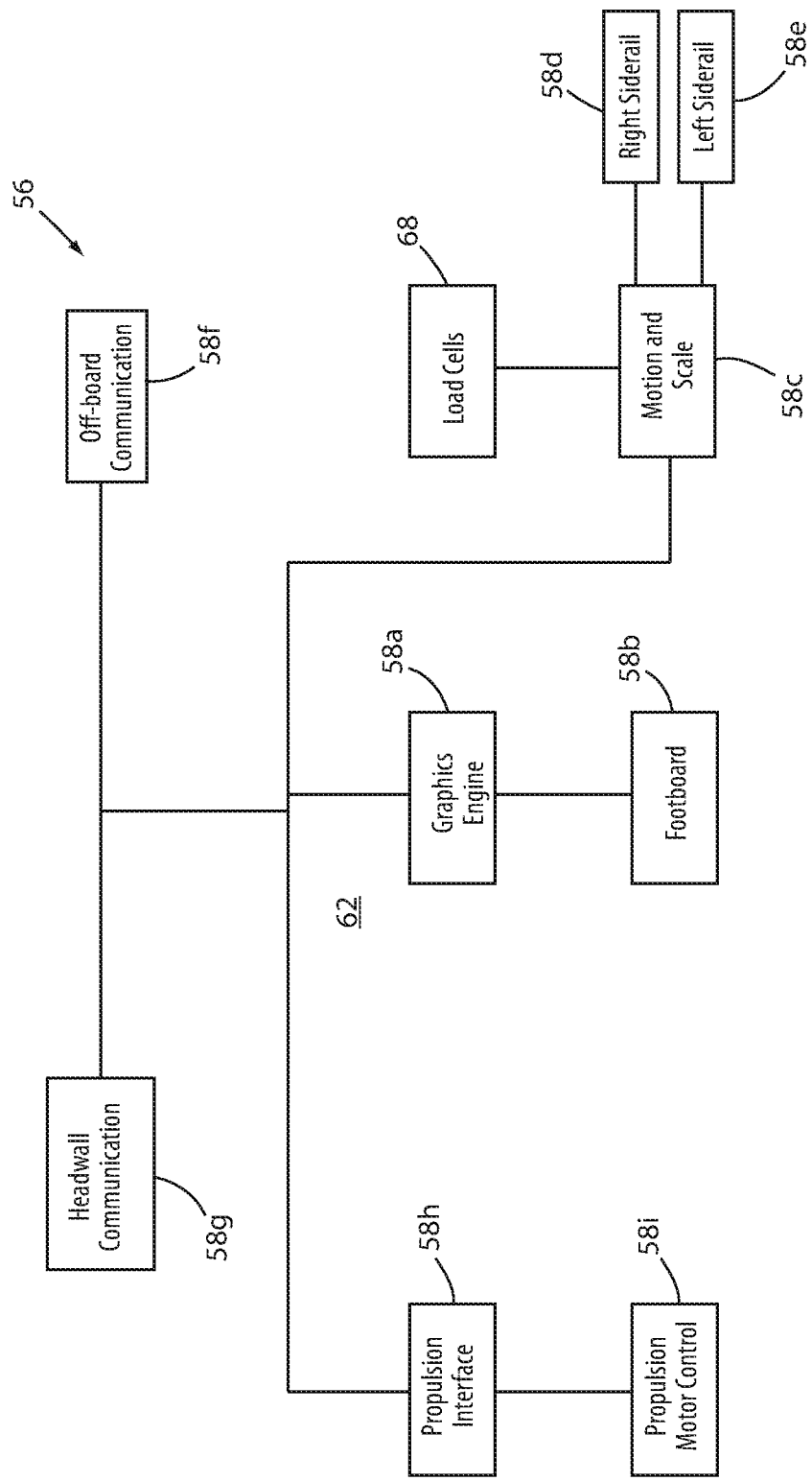
FIG. 2 is a block diagram of an illustrative control system incorporated into the patient support apparatus of FIG. 1.

FIG. 2 illustrates one example of a control system 56 for patient support apparatus 20. Control system 56 includes a plurality of nodes 58. Each of the nodes 58 is coupled to one or more other nodes by a communication medium 60. Together the nodes 58 and communication medium 60 form an embedded network 62. Each of the nodes performs specific functions that are described in more detail below. As will also be described in greater detail below, nodes 58 include electronic circuit boards that assist in one or more of the following: controlling the motion of various devices (pumps, motors and actuators); displaying information from the various devices or neighboring devices; providing user interfaces for input by users; measuring weights with an on-board scale system; communicating with a healthcare facility's network including its nurse call system; driving a device within the hospital environment by use of a manual user input, such as drive handles, or by receiving input via one or more load cells or strain gauges; receiving feedback or other sensor information from various devices using sensors; and receiving and transmitting data both onboard patient support apparatus 20 and off-board patient support apparatus 20.

Although FIG. 2 illustrates a specific architecture of control system 56 having a specific number of nodes 58 connected together in a specific way by a single communication medium 60, it will be understood that this particular architecture is only illustrative, and that control system 56 can be varied in terms of the number of nodes 58, their function, their connections to each other, and/or the use of one or more different communication media 60 used to couple the nodes 58 together. In some embodiments, embedded network 62 includes a plurality of different communication media and/or uses a plurality of different communication protocols, such as disclosed in commonly assigned U.S. patent application Ser. No. 62/464,565 filed Feb. 28, 2017, by inventors Krishna Bhimavarapu et al. and entitled PATIENT CARE DEVICES WITH ON-BOARD NETWORK COMMUNICATION, the complete disclosure of which is incorporated herein by reference.

Figure 3:
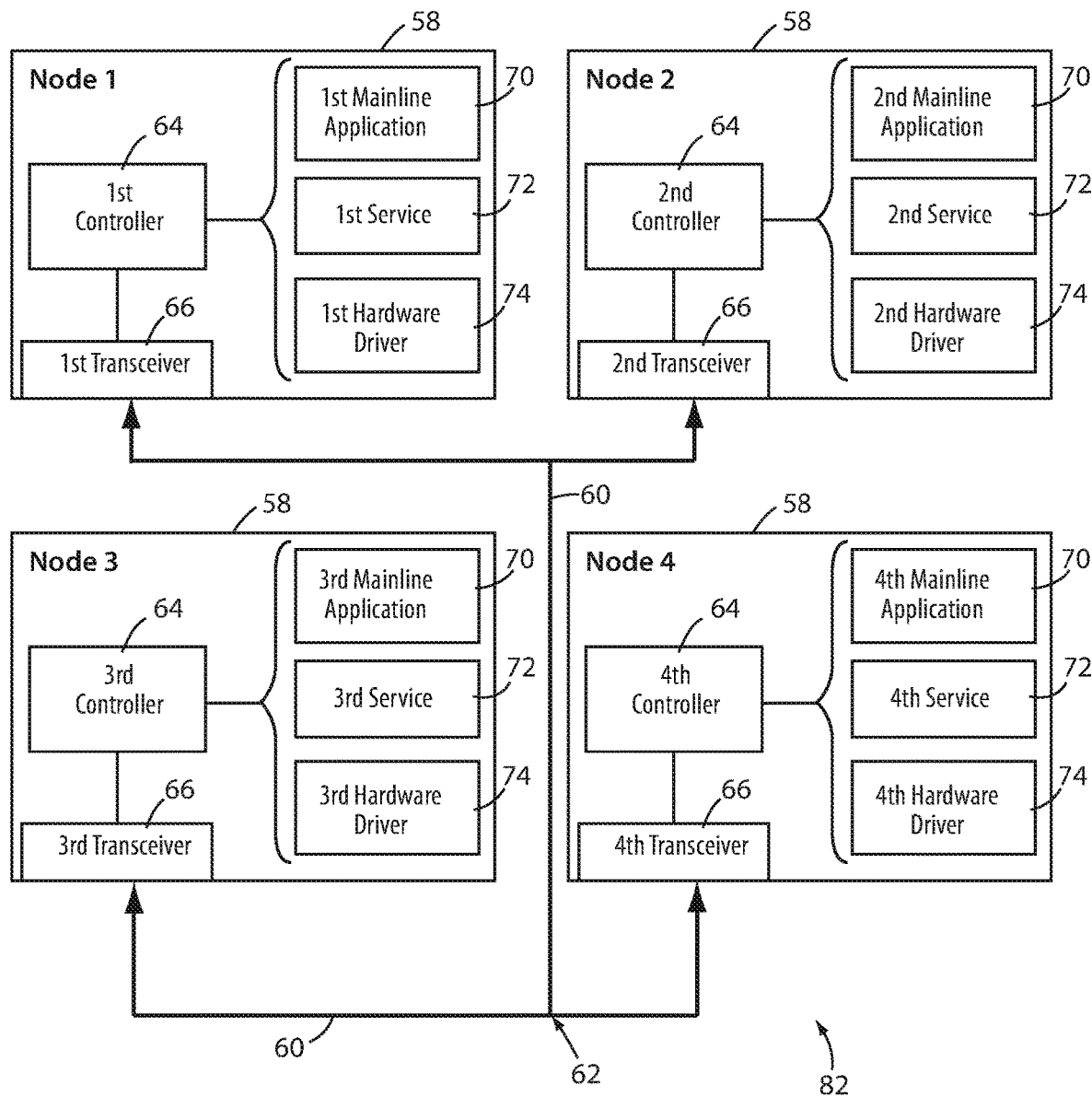
FIG. 3 is a block diagram of four arbitrary nodes of the control system of FIG. 2.

In the embodiment shown in FIG. 2, nodes 58 include a graphics engine node 58a, a footboard node 58b, a motion and scale node 58c, a right siderail node 58d, a left siderail node 58e, an off-board communication node 58f, a headwall communication node 58g, a propulsion interface node 58h, and a propulsion motor control node 58i. Each of the nodes 58 includes a controller 64 and a transceiver 66 (FIG. 3). The controllers are implemented as conventional microcontrollers in several embodiments. In a specific one of those embodiments, one or more of the controllers 64 are implemented as any one of the i.MX family of system-on-chip (SoC) processors which are marketed by Freescale Semiconductor of Austin, Tex. Other types of commercially available microcontrollers may also be used. Still further, the controllers may take on still other forms, such as any combination of any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by the controllers in carrying out the functions described herein, as well as the data necessary for carrying out these functions, are stored in one or more accessible memories (not shown).

The main functions carried out by each of the nodes 58 shown in FIG. 2 will now be described.

Graphics engine node 58a controls the graphics that are displayed on one or more displays of patient support apparatus 20. At least one such display is incorporated into footboard 34 and may be positioned adjacent, or integrated into, user interface 50. One or more additional displays may also be included, such as one or more displays mounted to siderails 36. In other embodiments, the display of footboard 34 is moved to a different location on patient support apparatus 20. In any of the embodiments disclosed herein, the display may be configured to function only as a display, or it may be configured as a touchscreen display that is sensitive to user touch.

Graphics engine node 58a includes memory for storing the graphics that are displayed on the one or more displays, as well as programming instructions for carrying out the display of those graphics. In some embodiments, graphics engine node 58a delivers graphics to the display that are organized in a scalable vector graphics (SVG) format. In other embodiments, graphics engine node 58a delivers graphics using another format.

Footboard node 58b (FIG. 2) oversees and controls user interface 50 of footboard 34. User interface 50, in at least some embodiments, includes a plurality of buttons for activating and deactivating motors used to move various components of patient support apparatus 20. In addition to controlling movement of patient support apparatus 20, user interface 50 also allows a user to take weight measurements of a patient supported on patient support apparatus 20, configure alert settings, and control other aspects of patient support apparatus 20. Footboard node 58b controls the communication between nodes 58 necessary to carry out the control of the motors, take weight readings, and configure alerts.

In some embodiments, a powered mattress is added to patient support apparatus 20 that is controllable via user interface 50. In those embodiments, footboard node 24b is in communication with the one or more buttons, or other controls, that are used to control aspects of the mattress. To carry out this control, footboard node 58b sends messages to the mattress over communication medium 60. These messages inform the mattress of which buttons and/or controls have been activated or deactivated by the user. In the configuration of control system 56 shown in FIG. 2, such messages pass from footboard node 58b to off-board communication node 58f, which is communicatively coupled to the mattress, either via a cable (e.g. a USB cable) or via a wireless connection. One example of such a wireless connection to the mattress is disclosed in commonly assigned U.S. Pat. No. 9,289,336 issued Mar. 22, 2016, to inventors Clifford Lambarth et al. and entitled PATIENT SUPPORT WITH ENERGY TRANSFER, the complete disclosure of which is incorporated herein by reference. Other types of wireless communication with the mattress may also be carried out.

Motion and scale node 58c (FIG. 2) controls the movement of patient support apparatus 20. Motion and scale node 58c therefore communicates directly with the motors incorporated into patient support apparatus 20. The motors carry out movement of various components of patient support apparatus 20, such as, but not limited to, the up/down movement of litter frame 28 whose height is adjustable with respect to base 22 by way lifts 26. Motion and scale node 58c also controls pivoting of various sections of support deck 30, such as head section 42 and, in some embodiments, one or both of thigh section 46 and foot section 48.

Motion and scale node 58c may also be configured to carry out one or more general operations of patient support apparatus 20. Such general operations include, but are not limited to, communicating with one or more indicators, such as any one or more lights, buzzers, displays, or the like that are able to provide an indication in aural or visual form to an occupant of patient support apparatus 20, or to a caregiver associated with patient support apparatus 20. Motion and scale node 58c may also communicate with one or more sensors that are adapted to detect parameters of patient support apparatus 20, such as, but not limited to, the status of a brake for wheels 24; the presence, absence, and/or movement of an occupant of patient support apparatus 20 on support deck 30; the height of support deck 30 relative to base 22; the status (raised or lowered) of one or more siderails 36; the armed or disarmed state of the exit detection system, and/or other parameters. For some indicators and/or sensors, node 58c is adapted to forward information from or to one or more of these indicators and/or sensors to one or more of the other nodes 58 of control system 56.

Motion and scale node 58c also controls a scale and exit detection subsystem. The scale and exit detection subsystem includes a plurality of load cells 68 that are positioned generally adjacent each corner of litter frame 28 and which are in direct communication with motion and scale node 58c. The load cells sense the amount of downward weight that is exerted by an occupant of patient support apparatus 20, as well as movement of the occupant. The outputs from the load cells are processed by motion and scale node 58c to determine the total weight detected, the distribution of the weight, and/or movement of the occupant of patient support apparatus 20. Motion and scale node 58c issues any appropriate alerts based on the outputs from load cells 68 and/or forwards the processed outputs from the load cells 68 to one or more other nodes 58 of control system 56 (e.g. off-board communication node 58f and/or headwall node 58g).

In at least some embodiments, motion and scale node 58c is constructed to carry out scale and/or exit detection functions in the manner disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, motion and scale node 58c is configured to operate in any of the manners disclosed in commonly assigned U.S. patent application Ser. No. 62/076,005 filed Nov. 6, 2014 by inventors Marko N. Kostic et al. and entitled EXIT DETECTION SYSTEM WITH COMPENSATION, or in commonly assigned U.S. patent application Ser. No. 62/065,242 filed Oct. 17, 2014 by inventors Marko N. Kostic et al. and entitled PATIENT SUPPORT APPARATUSES WITH MOTION MONITORING, the complete disclosures of both of which are hereby incorporated herein by reference. In yet another embodiment, motion and scale node 58c includes at least one signal acquisition node of the type disclosed in commonly assigned U.S. patent application Ser. No. 62/428,834 filed Dec. 1, 2016, by inventors Marko Kostic et al. and entitled PERSON SUPPORT APPARATUSES WITH LOAD CELLS, the complete disclosure of which is incorporated herein by reference. Still other types of scale and exit detection subsystems may alternatively be used.

Right and left siderail nodes 58d and 58e (FIG. 2) are integrated into the right and left head end siderails 36, respectively. Siderail nodes 58d and 54e control the occupant and caregiver user interfaces 52 and 54 integrated into the head end siderails 36. Nodes 58d and 54e forward commands entered through either of user interfaces 52 and 54 to motion and scale node 58c and/or to other nodes 58 of control system 56. Siderail nodes 58d and 54e also control one or more lights or other audio and/or visual indicators that are incorporated into user interfaces 52 and 54.

Off-board communication node 58f (FIG. 2) controls non-headwall communication between patient support apparatus 20 and one or more devices that are located off-board patient support apparatus 20 or that are separate devices from patient support apparatus 20 (e.g. a powered mattress or a medical device used in the treatment of a patient). Off-board communication node 58f thus acts as a gateway between the on-board control system 56 and one or more external devices. In many embodiments, off-board communication node 58f includes one or more wireless transceivers for wirelessly communicating with one or more external devices. In at least one embodiment, off-board communication node 58f includes a WiFi transceiver (IEEE 802.11) that enables wireless communication between patient support apparatus 20 and one or more wireless access points of a local area network, such as, but not limited to, a hospital Ethernet. In some embodiments, off-board communication node 58f includes a ZigBee and/or Bluetooth transceiver for communicating with one or more medical devices, or other devices, positioned within the vicinity of patient support apparatus 20. Off-board communication node 58f may also, or additionally include, one or more long-range RF transceivers and/or visible light transceivers for enabling wireless communication using visible light, such as is disclosed in more detail in commonly assigned U.S. patent application Ser. No. 62/430,500 filed Dec. 6, 2016, by inventor Michael Hayes et al. and entitled NETWORK COMMUNICATION FOR PATIENT SUPPORT APPARATUSES, the complete disclosure of which is incorporated herein by reference.

In some embodiments, off-board communication node 58f controls various aspects of a powered mattress positioned on patient support apparatus 20. The powered mattress may be an inflatable mattress that contains multiple air bladders whose inflation and deflation levels are controllable via user interface 50. In some embodiments, the powered mattress is any one of the mattresses sold under the brand names Isolibrium and/or XPRT by Stryker Corporation of Kalamazoo, Mich. In some embodiments, the powered mattress includes any one or more of the features described in commonly assigned U.S. patent application Ser. No. 13/836,813 filed Mar. 15, 2013 by inventors Patrick Lafleche et al. and entitled INFLATABLE MATTRESS AND CONTROL METHODS and/or commonly assigned U.S. patent application Ser. No. 14/308,131 filed Jun. 18, 2014 by inventors Patrick Lafleche et al. and entitled PATIENT SUPPORT COVER, the complete disclosures of both of which are incorporated herein by reference. In still other embodiments, still other types of mattresses may be used. The coupling of node 58f to the mattress may be carried out via a wired or wireless connection.

When a mattress is communicatively coupled to node 58f, it transmits status and other messages to footboard node 58b that provide an indication of the current state of one or more aspects of the mattress, such as, but not limited to, the current inflation pressure of one or more sections of the mattress, the state of any therapies that are currently being provided by the mattress, and/or other information about the mattress. Some of that information is selectively displayed by footboard node 58b on a display associated with user interface 50.

Headwall node 58g (FIG. 2) communicates with a headwall positioned within a room of a healthcare facility, such as a hospital. Such headwall communications enable patient support apparatus 20 to communicate with a conventional nurse call system that is in communication with the headwall, and/or a conventional room control system that controls one or more aspects of a patient's room (e.g. a television, a room light, curtains, temperature, etc.). Such communication may be wired or wireless. Headwall node 58g may also be adapted to communicate with individual location beacons that enable the location of patient support apparatus 20 to be determined based upon stored knowledge of the location of each of the individual beacons. One example of such location determination is described in more detail in commonly assigned U.S. Pat. No. 8,674,826 issued to Becker et al. and entitled LOCATION DETECTION SYSTEM FOR A DEVICE, the complete disclosure of which is hereby incorporated herein by reference.

Headwall node 58g also provides communication between patient support apparatus 20 and a conventional nurse call system by using, in at least one embodiment, a standard 37-pin nurse call cable adapted to communicate with a nurse call system interface. In addition to transmitting voice signals to and from the nurse call system, the standard 37-pin cable may further transmit alert information (e.g. whether an exit alert has been triggered or not), and/or other information to the nurse call system.

In some embodiments, headwall node 58g also or alternatively provides wireless communication between patient support apparatus 20 and a conventional nurse call system by using, in at least one embodiment, a Bluetooth transceiver adapted to wirelessly communicate with the nurse call system. More detailed description of several manners in which headwall node 58g may wirelessly communicate with nurse call system are disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of headwall communication may also be implemented.

Propulsion motor control node 58i (FIG. 2) controls a motor that powers and, in some cases, steers one or more of wheels 24, thereby easing the physical load otherwise experienced by a caregiver when moving patient support apparatus 20 from one location to another. In alternative embodiments, patient support apparatus 20 includes a separate wheel positioned generally in the middle of base 22 that is powered. Such powered wheels are disclosed in commonly assigned U.S. patent application Ser. No. 62/315,067 filed Mar. 30, 2016, by inventors Thomas Puvogel et al. and entitled PATIENT SUPPORT APPARATUSES WITH DRIVE SYSTEMS, the complete disclosure of which is incorporated herein by reference. In alternative embodiments, propulsion motor control node 58i controls the motors for any of the propulsion systems disclosed in commonly assigned U.S. patent application Ser. No. 13/795,193, filed Mar. 12, 2013, by inventors Richard Derenne et al. and entitled POWERED PATIENT SUPPORT APPARATUS, and/or in U.S. Pat. No. 6,772,850 issued to Waters et al. and entitled POWER ASSISTED WHEELED CARRIAGE, the complete disclosures of both of which are hereby incorporated herein by reference. Other types of on-board propulsion systems may also be controlled by propulsion motor control node 58i.

When propulsion motor control node 58i is included on patient support apparatus 20, propulsion interface node 58h is also provided and controls and oversees a propulsion user interface (not shown). The propulsion user interface includes the controls used by a person to operate the propulsion system. In some embodiments, the user interface includes a pair of handles having force sensors that detect forces applied by a user. One example of such handles and force sensors are disclosed in the aforementioned commonly assigned 62/315,067 patent application. Propulsion interface node 58h senses the magnitude and, in some cases the direction, of the applied forces and sends messages indicating the sensed magnitudes and directions to propulsion motor control node 58i. Propulsion motor control node 58i, in response, sends motor controls commands to the one or more propulsion motors.

Nodes 58a-i communicate with each other over communication medium 60. Communication medium corresponds to the physical layer (layer 1) of the Open Systems Interconnection (OSI) Model, and includes the wires, cables, cords, fiber optics, etc. that couple the nodes 58 together. Communication medium 60 may take on a variety of different forms, such as, but not limited to, one or more Cat 5 cables, one or more Controller Area Network (CAN) cables, one or more RS-485 cables, one or more I-Squared-C ($I^2C$) cables, and/or one or more other types of cables, wires, or other connectors. In some embodiments, embedded network 62 may include one or more Ethernet switches that communicatively couple different nodes 58 together. One such embedded network is disclosed in commonly assigned U.S. patent application Ser. No. 14/622,221 filed Feb. 13, 2015, by inventors Krishna Bhimavarapu et al. and entitled COMMUNICATION METHODS FOR PATIENT HANDLING DEVICES, the complete disclosure of which is hereby incorporated herein by reference. Other types of embedded networks 62 may also be used.

The particular messages communicated over network 62 convey a plurality of different types of information. In general, the messages includes any commands, sensors readings, status information, alerts, and/or other types of data that are generated or used by any of the nodes 58 when carrying out the functions described above. Messages are thus transferred between nodes 58 when a user or caregiver pushes a button (or otherwise activates a control) that moves a component of patient support apparatus 20, when a caregiver changes one or more settings of patient support apparatus 20 (e.g. arms or disarms the exit detection system, takes a weight reading, locks out a patient's motion and scale interface, etc.), when new readings are taken from one or more sensors, and/or when other information needs to be communicated. Regardless of the specific content of the messages, the messages are transmitted between nodes 58 as one or more packets.

Messages that are commonly passed between headwall node 58g and a conventional nurse call system and/or between off-board communication node 58f and a local area network of a healthcare facility include the following: messages indicating that an occupant of patient support apparatus 20 has exited, or is about to exit, from patient support apparatus 20; messages to turn on or off one or more room lights; messages to turn on or off one or more reading lights; messages to increase or decrease the volume of a nearby television set; messages to change a channel of the nearby television set; messages containing audio packets generated from one or more microphones on the patient support apparatus 20 into which an occupant of patient support apparatus 20 speaks when desiring to communicate with a remote caregiver; messages indicating the current status of one or more siderails 36 of patient support apparatus 20 (e.g. whether the side rails are up or down, or have changed position); messages indicating the current status of a brake on patient support apparatus 20; messages indicating the current status of the height of support deck 30 relative to base 22 (e.g. such as whether support deck 30 is at its lowest height or not); messages indicating the current angle of head section 42 with respect to horizontal; messages indicating the current status of an exit detection system (e.g. whether an exit detection system is armed or not); messages indicating the current charging status of one or more batteries on patient support apparatus 20; messages indicating the current status of an alternating current (A/C) power cable on patient support apparatus 20 (e.g. whether it is plugged in or not); diagnostic information about patient support apparatus 20; and/or any other messages containing information about patient support apparatus 20 which may be useful to communicate to a remote location. Such messages originate from, or are destined to, one or more of the nodes 58 of patient support apparatus 20.

Figure 4:
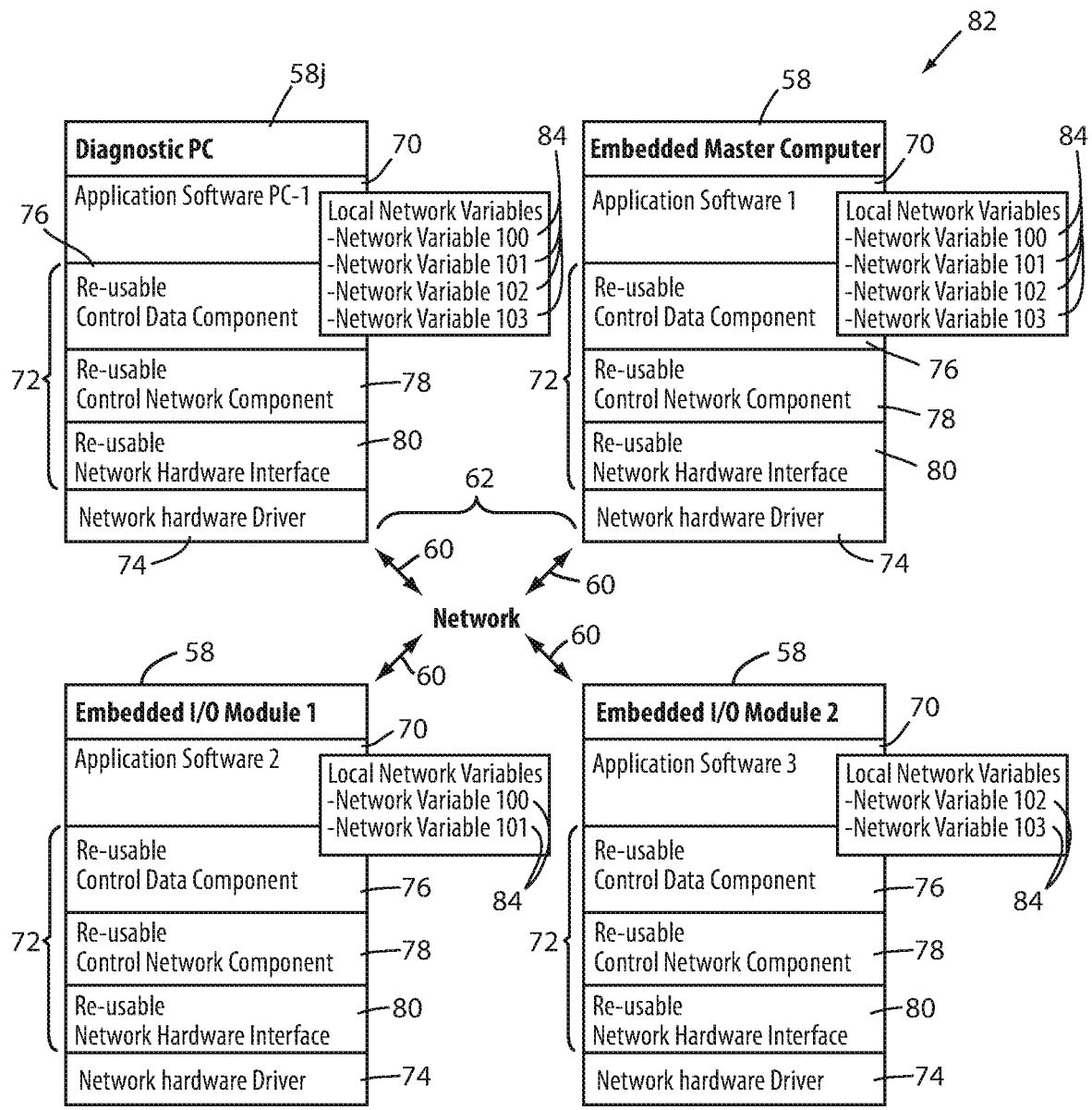
FIG. 4 is a block diagram of the software components of a plurality of arbitrarily selected nodes of the control system of FIG. 2, shown with a diagnostic computer coupled to the network.

FIGS. 3 and 4 illustrate four of the nodes of FIG. 2 that have been arbitrarily selected in order to better understand the control and communication system of the present disclosure. The four nodes 58 shown in FIGS. 3 & 4 have not been specifically identified with respect to the nodes 58*a*-*h* shown in FIG. 2 in order to convey the fact that the principles of the present disclosure can be carried out with respect to any of the nodes 58*a*-*h* of FIG. 2, as well as other types of nodes. Also, the selection of four nodes in FIGS. 3 & 4, rather than all of the nodes shown in FIG. 2, is meant to convey the fact that the principles of the present disclosure can be incorporated into communication networks having a different number of nodes 58 than what is shown in FIG. 2 (as well as fewer or greater than the four nodes shown in FIGS. 3 & 4).

As shown in FIG. 3, each of the controllers 64 of nodes 58 of embedded network 62 is programmed to execute one or more mainline software applications 70 and one or more services 72. Each node 58 also includes an appropriate network hardware driver 74 adapted to carry out communications over the particular communication medium 60 (physical layer) used in embedded network 62, as well as, in some cases, the specific layer 2 (data link layer) formatting used by embedded network 62. The mainline software applications 70 may, and typically do, vary for each node 58 according to the particular functions carried out by that particular node. Many of these functions were described above. Each service 72 is adapted to carry out background sharing and updating of network variables among the various nodes 58 in a manner that will be described in greater detail below.

Each of the services 72 may include one or more components, such as the individual components illustrated in FIG. 4. As shown therein, each service 72 includes a control data component 76, a control network component 78, and a network hardware interface 80. The combination of these components 76-80 in each of the nodes, as well as their interaction with mainline applications 70, drivers 74, and communication medium 60 creates a transparent communication system 82 that provides a simple and universal mechanism for communicating information between nodes 58 on network 62. Communication system 82 is designed to operate on any microprocessor/controller running any operating system and can operate on top of any arrangement or configuration of physical and/or data link layers.

Transparent communication system 82 provides three main functions: a common operating environment management, data sharing via network variables, and storage of persistent device data. The operating environment of transparent communication system 82 also contains various timing and other utility subroutines, which may be used to create a standalone non-pre-emptive operating system scheduler, if desired. The same communication technology can be easily used on top of any other operating system or scheduler environment.

The data sharing function of transparent communication system 82 allows for each mainline application 70 to communicate information to other connected nodes 58 over network 62 without even needing to know that there is a network connected to the node 58 on which that mainline application 70 is executing. If network 62 grows, new data points can be trivially added as needed without harming any of the existing data communications and without requiring rewriting or modifying any of the mainline applications 70.

The persistent data storage function of system 82 allows for a consistent methodology of storing and retrieving data that must survive a power loss. This data includes such things as software versions, configurations, event logs, operating states and calibration values.

Each of the nodes 58 in network 62 are uniquely identified by a device ID. In the illustrated embodiment of system 82, the device ID is an 8-bit value (range 0 to 255), but it will be understood that different lengths and/or types of device IDs may be used. In at least one embodiment, all of the device IDs with a value of less than ten are reserved for system use. Other ranges may be reserved for system use.

Transparent communication system 82 is adapted to manage and share constructs referred to herein as network variables 84 (FIG. 4). Network variables 84 can contain data of varying sizes, such as, but not limited to, the following: 1-bit (e.g. on/off flags); 2-bit (values from 0 to 3); 4-bit (values from 0 to 15); 8-bit (e.g. values from 0 to 255); 16-bit (e.g. values from 0 to 65,535); 24-bit (e.g. 0 color values, high resolution sensor values); 32-bit (e.g. values from 0 to 4,294,967,295); and Binary Large OBjects (BLOBs) (e.g. text strings, complex data, software update packets).

In some embodiments, one or more network variables 84 are used to contain a sensor reading or a text string message to be displayed on a user interface, such as any of user interfaces 50, 52, and/or 54. For example, sensor readings include, but are not limited to, weight readings from load cells 68, button presses or switch activations from any of user interfaces 50, 52, and 54, current height readings of litter frame 28, status updates of a brake for braking wheels 24, the armed or disarmed status of an exit detection system, actuator or motor readings, one or more communication settings, etc.

Each network variable 84 is uniquely identified on the network 62 by a network variable ID (netVar ID), which will be described herein as being a 12-bit ID with a range 0 to 4095, although it will be understood that IDs of different length may be used. At the system level, all netVar IDs are created by the system architect. Typically, network variables 84 are broken into two classifications. The first classification is common network variables 84 that may be used by multiple nodes 58 on network 62. For example, these common network variables 84 might store values representing current system operating modes, or power monitoring information that could affect all nodes 58.

The second classification is node-specific network variables 84. During the system-level network variable definition, each type of node 58 on the network is usually assigned a range of network variable IDs. For example, nodes 58 categorized as type A might be assigned IDs 1000 to 1049 (50 possible values) and nodes 58 categorized as type B might be assigned IDs 1700 to 1724 (25 possible values). The different node types may refer to nodes that perform different functions. For example, type A nodes might refer to nodes 58 that handle the operation of a siderail 36 (e.g. nodes 58*d* and 58*e* in FIG. 2), while type B nodes might refer to nodes 58 that handle a propulsion system of a patent support apparatus (e.g. node 58*i* in FIG. 2). The node types may refer to not only the specific nodes 58 that perform a particular function within a particular patient support apparatus 20, but may refer to multiple different nodes 58 that perform the same function. For example, a first node 58 on a first patient support apparatus that controlled a first siderail 36 having a built-in touch-screen and a second node 58 on a second patient support apparatus that controlled a second siderail 36 having no built-in touch screen might both be classified as type A nodes 58 because they both control patient support apparatus siderails 36, albeit different types of siderails 36.

Regardless of the classification of the nodes 58, each of the nodes 58 of network 62 are presented with all available data from the other nodes 58. There is no selective routing of information through network 62. This broadcast architecture greatly simplifies the design of a distributed control architecture using transparent communication system 82.

Depending upon the specific design of patient support apparatus 20, system 82 may contain hundreds or even thousands of network variables 84. A given node 58 on the network is typically only interested in the contents of a small number of them. To prevent a node 58 from experiencing information overload with unnecessary information, each node 58 only listens for those network variables 84 that are of interest to it. All other network variables 84 that are broadcast over network 62 are ignored by that particular node 58. The process of selecting which network variables 84 are to be utilized by a particular node 58 is known as registering a network variable with that particular node 58. When registering a network variable 84 with a particular node, only the network variable ID and the type of data represented by that network variable (e.g. 1-bit or 8-bit) is needed.

Network variables 84 are registered the same, regardless of whether the network variables 84 are inputs or outputs to or from a particular mainline application 70. They both use the same data management technology and they are both registered in the same way. In some embodiments, by default, all registered network variables 84 always receive updated values from the network 62 (inputs). If a node 58 wishes to share the information contained in a specific network variable 84 with other nodes 58 (output), it can set the network variable 84 in question to be either "TRANS-MIT_ONCE" or "TRANSMIT_ALWAYS". If the node 58 is to stop sharing the information in a particular network variable 84, the controller 64 of the node sets the network variable 84 in question to be "TRANSMIT_NEVER", which effectively turns the network variable 84 back to input-only.

In some embodiments, the type of network variable 84 must be the same between the sender node 58 and the receiver node 58. For example, if the sending node 58 registers a network variable 84 with a netVar ID of 1000 as a 1-bit type, and the receiving node 58 registers the network variable 84 with netVar ID 1000 as an 8-bit type (i.e. the data types are mismatched), the mainline application 70 of the receiving node 58 will not receive the value.

An elegant feature of communication system 82 is the abstraction of the data communicated via network 62 from the underlying network 62 itself. Using a network variable 84 from a remote node 58 within a mainline application 70 of a local node 58 is as simple as reading from a global variable. Changing a network variable 84 in a local mainline application 70 in a manner that shares the changed value with all other nodes 58 interested in that particular variable 84 is as simple as writing to a global variable.

Network communication in communication system 82 occurs "behind the scenes" in either an interrupt or scheduled context. The mainline software application 70 of each node 58 sees none of the network and protocol interactions actually required to send information between nodes 58. This simplifies the design and reduces the complexity of each of the mainline applications 70.

Because each network variable 84 is a global variable within a software context, and because there is no direct software interaction by mainline application 70 with receiving data from network 62 within system 82 (i.e. it happens transparently to the mainline applications 70), there is no way for a mainline application 70 to inherently determine whether the data present in a particular network variable 84 is 1 millisecond old, or 1 hour old. To address this, each write to a network variable 84 performed by service 72 also updates a corresponding network variable timestamp. Associated with each particular network variable 84 is a threshold value (defined by the software developer) stating how long that particular network variable 84 can be considered valid in the absence of any new data being received. A comparison of the difference between the "last write" timestamp and the current system time indicates how old the data or value of a particular network variable 84 is. If this difference is greater than the threshold set by the developer, a simple query through system 82 as to whether or not it is "goodToUse" will report that it is no longer good too use. Table 1 below illustrates an example of this time stamping and staleness determination for two arbitrary network variables 84: netVar1 and netVar2. As shown therein, netVar1 had its value updated recently enough to still be good to used according to its staleness threshold, while netVar2 had is value updated too long ago to meet its staleness threshold.

TABLE 1

| Timestamping system_time = 5000 ms | |
| --- | --- |
| netVar1 | netVar2 |
| value = 1 | value = 25 |
| write_timestamp = 4000 ms | write_timestamp = 2000 ms |
| stale_threshold = 2000 ms | stale_threshold = 1000 ms |
| (last written 1000 ms ago) | (last written 3000 ms ago) |
| (can tolerate up to 2000 ms) | (can tolerate up to 1000 ms) |
| value 1 is good to use! | value 25 should not be used |

The timestamping mechanism is useful in several ways. First, it can be used to allow communication failures to be tolerated such that a single missed message does not trigger a warning. Second, this mechanism can be used to determine if a network variable 84 is currently present on the bus (e.g. network 62). This is useful in situations like fault reporting where, under normal circumstances, the fault is not present. Since the fault is not present, it is most efficient to simply have the network variable 84 set as "TRANSMIT_NEVER" since that results in no bus traffic on network 62 at all. A "goodToUse" check on the network variable 84 would report that it is not good (i.e. no fault is present). If the fault were to become present, the network variable 84 could be set as "TRANSMIT_ALWAYS" resulting in data being transmitted on the bus. A "goodToUse" check would result that is good (i.e. fault is present) and appropriate action can then be taken.

One of the risks of interrupt or task-based software comes when multiple pieces of simultaneously-running software contend for the same resource. In the case of communication system 82, the resources of contention are the global variables used by each mainline application 70 to hold the values of the network variables 84. For example, if a mainline software application 70 is starting to read a text string value of a particular network variable 84, and during that read process, the mainline application 70 is interrupted when a changed value of that same network variable 84 is received via network 62, this could lead to an undesired outcome. Specifically, if the mainline application 70 were to continue its read from the global variable corresponding to the changed network variable 84, what would be seen by the application 70 is that the first portion of the network variable string (i.e. pre-interrupt) would contain the old data, and the second portion (i.e. post-interrupt) would contain the new data. Clearly this is not a desirable situation.

Communication system 82 addresses this potential problem by maintaining two copies of each network variable 84. That is, each node 58 stores a public copy that can be read and modified at will by service 72, and a private copy that only the mainline software application 70 can read or modify at will. The public and private copies of each network variable 84 are independent. Network 62 never touches the private value of a network variable 84 and the mainline software applications 70 never touch the public value of a network variable 84.

Figure 5:
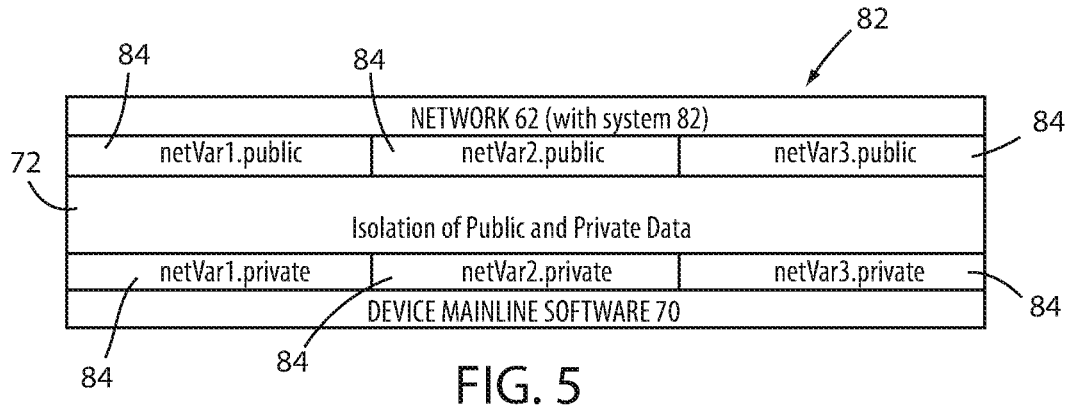
FIG. 5 is a diagram illustrating the separation of public and private network variables used in one embodiment of a communication system according to the present disclosure.

The isolation of the private and public values of three network variables 84 is illustrated in more detail in FIG. 5. Three illustrative network variables 84a, b, and c are illustrated therein. Services 72 coordinate communication between the values of network variables 84. That is, if a particular node 58 receives an updated value of netVar2 over network 62, the service 72 of that particular node 58 writes the new received value into the public netVar2 stored on that particular node 58. Conversely, if a particular node 58 wishes to update the value of the public netVar 2 on other nodes 58 within network 62, service 72 sends the value of its public netVar2 over network 62 to the other nodes 58, and the services 72 present on each of those nodes update their respective public values of netVar2 to be equal to the transmitted public netVar2. The transmission of new values of network variables 84 to other nodes 58 does not, in and of itself, change the value of any private network variables 84. Instead, communication of a variable's new value from a node 58 to network 62, as well a communication of a variable's new value from network 62 to a node 58, occurs via the public network variables 84. On the other hand, communication of new values to or from a mainline software application 70 occurs via private network variables 84, as described below.

Figure 6:
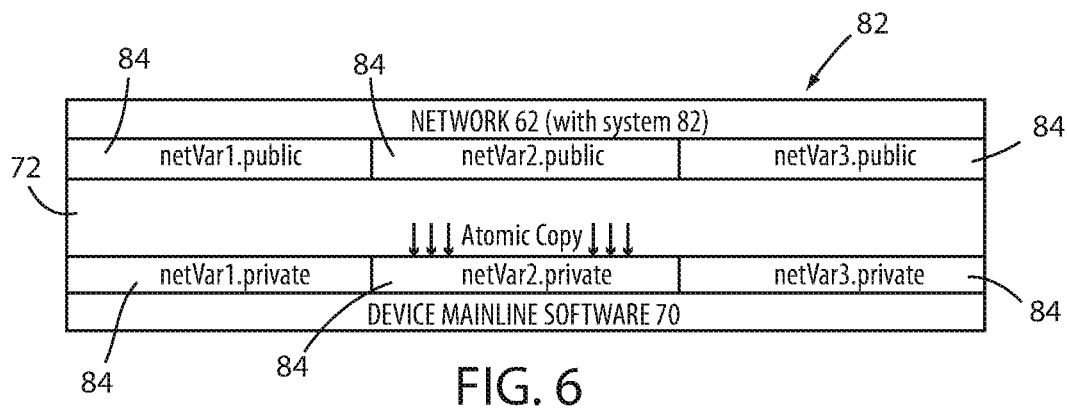
FIG. 6 is a diagram illustrating values of public network variables being copied into corresponding private network variables by the communication system of FIG. 5.

At prescribed times during the execution of mainline application 70 for each node 58, the service 72 copies the current values of the public network variables 84 to the private network variables 84. This allows the mainline application 70 to see the most recent value of each of the network variables 84 that are registered for that particular node 58. This process is shown in more detail in FIG. 6 for an arbitrary node 58. As shown therein, service 72 atomically copies the values of each of the public network variables 84 into the corresponding private network variables 84 used by mainline application 70 for that particular node.

Figure 7:
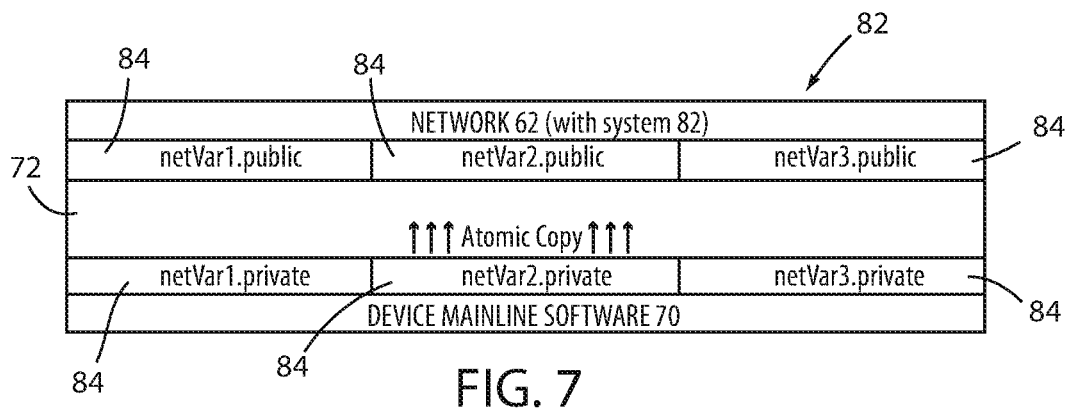
FIG. 7 is a diagram illustrating values of private network variables being copied into corresponding public network variables by the communication system of FIG. 5.

FIG. 7 illustrates the reverse process. That is, FIG. 7 illustrates service 72 copying the current values of the private network variables 84 into the public network variables 84 so that the network 62 and its other nodes 58 can see any changes that have been made to the network variable data. In other words, if and when a mainline application 70 changes a value of one or more its private network variables 84, service 72 uses these updated values of the private network variables 84 to reset the corresponding public variables 84 maintained on that particular node 58. Further, the service also shares these updated public network variables 84 with network 62 so that all other nodes 58 that have registered those particular variables 84 have the values of those variables updated. In this manner, when a single mainline application 70 updates its private network variables, the updated values of those private network variables are transparently shared by service 72 with all other nodes on network 62. As noted, this occurs without mainline application 70 being programmed to carry out any network communication.

The automatic updating of network variables 84 across network 62 allows each mainline application 70 of each node 58 to be programmed as if all of the variables it uses are purely local to that particular node 58. For example, consider a network variable 84 that indicates the current weight reading from load cells 68. This weight reading corresponds to the amount of weight currently being exerted on the litter frame 28 of patient support apparatus 20. This current weight reading is calculated by motion and scale node 58c based on the outputs from load cells 68. After this weight reading is calculated, the mainline application 70 executed by controller 64 of scale and motion node 58c sets its private weight variable (arbitrarily called netVarWeight herein for descriptive purposes) equal to the latest calculated weight reading. Service 72 of node 58c copies the private value of netVarWeight into a corresponding public netVarWeight variable 84 maintained at node 58c at designated times. Service 72 further transmits the updated public value of the netVarWeight variable 84 from node 58c to network 62. All those nodes 58 on network 62 that have the netVarWeight variable registered pick up this transmission and reset their public netVarWeight variables equal to the updated value that was transmitted from node 58c.

Thus, for example, in some patient support apparatuses, propulsion node 58i registers the netVarWeight variable in order to better assess how much power to apply to the propulsion motors (higher weights generally require greater power to move patient support apparatus 20, while lower weights generally require less power to move patient support apparatus 20). In such cases, the mainline application 70 executed by propulsion node 58i doesn't need to be programmed with instructions for asking a particular node, such as node 58c, for current weight readings. As a result, mainline application 70 of propulsion node 58i does not need to include all of the detailed programming necessary for communicating up-to-date data between itself and scale node 58c. Instead, mainline application 70 of propulsion node 58i simply reads the value of its private netVarWeight variable 84 and uses that value to control the propulsion of patient support apparatus 20. As far as the programming of mainline application 70 of propulsion node 58i, this process appears as if the "weight" variable (netVarWeight) were a variable that was local to node 58i, when in fact the value of that variable comes from scale node 58c. Mainline application 70 of propulsion node 58i, as well as the mainline applications 70 of all of the other nodes 58 that have registered the netVarWeight variable 84, can therefore all be programmed as if the netVarWeight variable 84 used in their execution resides locally.

The same is true for all other network variables 84. That is, all network variables 84 appear to be local to each of the mainline applications 70, and this local appearance applies in terms of both reading values and updating values. In other words, mainline applications 70 need not include any programming for retrieving a value of a particular network variable 84 from another node, or any programming for transmitting a value of a particular network variable 84 to one or more other nodes. Instead, this is all carried out by the services 72 on each node 58.

The copying of private variables to public variables, and vice versa, performed by service 72 can be facilitated with simple calls to the system code of system 82 from the mainline software application 70 whenever the mainline software application 70 deems it necessary. Services 72 perform atomic copies of the required data at these times to ensure data integrity. To further assure a deterministic system, this atomic copying activity may also be coordinated with a system-wide synchronization activity, such as is discussed in greater detail below.

The copying, updating, and maintenance of network variables 84 in communication system 82 can be better understood with an example of one manner in which the software executed by a controller of a node 58 can be programmed. It will be understood that this description is merely illustrative for a specific example of network variables 84, and that different network variables are additionally used in communication system 82. Further, it will be understood that each node 58 of communication system 82 utilizes similar type programming with the exception that different nodes have different network variables registered and different nodes 58 typically have different mainline software application 70 installed. Service 72, however, is generally the same for each node.

Consider the case where the readings from two of load cells 68 are assigned by a scale node 58*c* to two different network variables 84 called "LocalVarLoadCell1" and "LocalVarLoadCell2." From a system level, these two network variables are assigned to specific network variables number, such as netVar100 and netVar101, respectively. In one embodiment, each of these network variables 84 is selected to have a size of 24 bits, although other sizes may be used. After these two network variables have been assigned to netVar100 and netVar101, service 72 of node 58*c* is programmed in the following pseudocode manner:

Perform network setup and other hardware-specific things (baud rate, etc.)
    Register the network variables (netVar100 and netVar101)
        Call "LocalVarLoadCell1=AddNetVar(100.24 bit, BroadcastAlways)"
        Call "LocalVarLoadCell2=AddNetVar(101.24 bit, BroadcastAlways)"

The registering of the network variables for node 58*c* is performed by the service 72 executed by controller 64 of node 58*c*. Mainline application 70 of node 58*c* chooses which of the multitude of network variables 84 it needs to use in the performance of its tasks. To register those selected network variables 84, mainline application 70 of node 58*c* submits a request to its service 72 to register those network variables 84 of interest. Within service 72 is a lookup table of all the currently registered network variables 84 for node 58*c*. This list is maintained by service 72 completely separately from mainline application 70 of node 58*c*.

As defined by the code of mainline application 70 of node 58*c*, the main operating system or scheduler loop of node 58*c* performs the tasks described in pseudocode:

Call "Accept Network Variables From Remote Systems" (a general call that applies to all network variables and protects against concurrency problems)
    Acquire load cell readings
    LocalVarLoadCell1.private_value=reading for load cell 1
    LocalVarLoadCell2.private_value=reading for load cell 2
    any other program code that mainline application 70 of node 58*c* executes, including, but not limited to, using other network variables 84
    Call "Commit Network Variables to Remote Systems" (a general call that applies to all network variables 84 and protects against concurrency problems)

The calling of the "Accept Network Variables From Remote Systems" copies the current public values of LocalVarLoadCell1 and LocalVarLoadCell2 into the private network variables used by mainline application 70. Mainline application 70 then acquires the load cell readings from the first and second load cells 68. After acquiring these readings, mainline application sets the private network variables LocalVarLoadCell1 and LocalVarLoadCell2 equal to the latest load cell readings. Thereafter, mainline application calls the "Commit Network Variables to Remote Systems" function, which causes service 72 to copy the latest private values of LocalVarLoadCell1 and LocalVarLoadCell2 into the public variables netVar100 and netVar101. Service 72 then shares these variables netVar100 and netVar101 with network 62. The actual transmission and reception of netVar100 and netVar101 is done completely in the background of mainline application 70 and is independent of the scheduler loop of controller 64 of node 58*c*.

One or more other nodes 58 of communication system 82 utilize the outputs from load cells 68. In addition to, or in lieu of, propulsion node 58*i* discussed above, the outputs of the load cells may be communicated off-board patient support apparatus 20 via off-board communication node 58*f*. Communication node 58*f* (or any other node 58 utilizing netVar100 and netVar101) processes the updated values of netVar100 and netVar101 in accordance with the following pseudocode, which is executed by controller 64 of node 58*f*:

Perform network setup and other hardware-specific things (baud rate, etc.)
    Register the network variables
        Call "LocalVarLoadCell1=AddNetVar(100.24 bit, BroadcastNever)"
        Call "LocalVarLoadCell2=AddNetVar(101.24 bit, BroadcastNever)"

These steps are carried out by service 72 of node 58*f*. Mainline application 70 of node 58*f* performs the following pseudocode operations:

Call "Accept NetVars From Remote Systems" (a general call that applies to all network variables and protects against concurrency problems)
    Transmit localVarLoadCell1.private_value off-board (or do something else with it)
    Transmit localVarLoadCell2.private_value off-board (or do something else with it)
    Any other program code that mainline application 70 of off-board communication node 58*f* executes using any network variables 84
    Call "Commit NetVars to Remote Systems" (a general call that applies to all network variables and protects against concurrency problems)

The actual reception of netVar100 and netVar101 by node 58*f* is done completely in the background, and is independent of the scheduler loop of node 58*f*. If embedded network 62 utilizes a simple serial based communication protocol (e.g. RS-485, I²C, etc.), when node 58*f* receives a hardware interrupt indicating that data has been received, it concatenates each piece of data together until a packet has been received (this is a data link layer activity). Once a full and valid packet has been received, service 72 decodes it into individual network variables (e.g. netVar100 and netVar101 in this case). If embedded network 62 utilizes a conventional packet based communication system, such as Ethernet or TCP, and node 58*f* includes an operating system, the operating system builds up packet data in the background using its own means. Service 72 monitors to see if a complete packet has been received. When the packet is fully built, the operating system triggers an event within service 72 and the packet is decoded into individual network variables (e.g. netVar100 and netVar101 in this case). If embedded network 62 uses an existing message based communication system (e.g. Controller Area Network), when node 58f receives hardware interrupts indicating that a message has been received (which might typically be just one network variable, or in the case of BLOB data, a partial network variable), it is passed to service 72 to be decoded into a network variable.

As described above, regardless of the specific type of existing communication protocol used with embedded network 62, after node 58f receives the updated values of the load cell readings, it copies the received public values into the corresponding private network variables utilized by mainline application 70 of node 58f. Mainline application 70 uses these values without having to perform any of the transmission and receipt tasks, which are carried out in the background by service 72.

Communication system 82 is constructed to allow system designers to assure that certain activities occur at the same time on multiple nodes 58 across network 62. For example, it is often desirable to have all nodes 58 take a snapshot of their sensor readings at the same time. Some nodes 58 may take longer to complete the snapshot process than others. One way to utilize communication system 82 to achieve sensor reading synchronization is to use a network variable 84, such as one that will be referred to herein as NetVarSync. NetVarSync can be set to any value from 0 to 255 and broadcast by all nodes 58 simultaneously. All receiving nodes 58 can be set to monitor or wait for a particular value of NetVarSync at which time they can all take the appropriate action. Assignment as to what each NetVarSync value represents is done during the system level design. For example, when a value of 0 is received via NetVarSync, all nodes 58 begin acquiring data from their sensors, in one embodiment. Additionally, or alternatively, when a value of 1 is received via NetVarSync, all nodes 58 begin processing their data. An example of this process is shown below in Table 2.

(or other data integrity content). In some embodiments, each packet is a small as six bytes in length, although other packet lengths may also be used.

The packets transmitted by communication system 82 fit into different places within the OSI level of network hierarchy, depending upon the particular implementation within patient support apparatus 20 (or another patient care device). Each packet is essentially "piggybacked" on top of the underlying protocol used by the particular conventional network technology selected for implementation within patient support apparatus 20. This allows system 82 to take full advantage of the features offered by the advanced conventional protocols when they are available. If no advanced protocol is available, system 82 can be implemented to stand on its own within the OSI model. Examples of the different OSI mapping of the packets of system 82 can be seen in the following descriptions of four different types of networks 62: (1) simple serial networks; (2) packet-based network with bus contention detection; (3) packet-based networks with advanced network stacks; and (4) message based networks.

If embedded network 62 consists of communication media 60 that define a simple serial network with no network stacking, such as, but not limited to, RS-232, RS-422, RS-485, SPI, I$^2$C and others, communication system 82 is still able to carry out its functions over such networks. One of the characteristics of these type of serial communication networks is that only one node 58 can transmit on the bus (medium 60) at a time. Communication system 82 provides a mechanism to control which node is able to transmit at any given time in such a system. In one embodiment, the bus control mechanism is a token passing mechanism. In this embodiment, one centralized node 58 known as the "arbiter" (device ID 1, in some embodiments) holds the token on startup. If redundancy is desired, a second centralized node known as the backup arbiter (e.g. device ID 2) can hold the

TABLE 2

Node Synchronization

| Schedule time (ms) | deviceID1 (arbiter) | deviceID3 | deviceID10 | deviceID20 |
|---|---|---|---|---|
| 0 | | (wait for sync 0) | (wait for sync 0) | (wait for sync 0) |
| 10 | NetVarSync = 0 | Acquire data | Acquire data | Acquire data |
| 20 | | (wait for sync 1) | | |
| 30 | | | | (wait for sync 1) |
| 40 | | | (wait for sync 1) | |
| 50 | NetVarSync = 1 | Process data | Process data | Process data |
| 60 . . . 100 | . . . | . . . | . . . | . . . |

Communication system 82 is network independent. It doesn't matter whether network 62 is implemented using a simple I$^2$C serial bus, for example, or whether network 62 is an Ethernet or a Controller Area Network (CAN) network. Communication system 82 carries out broadcasting of network variables 84 to all nodes 58 in a deterministic manner regardless of which specific type or types of embedded networks 62 are implemented in patient support apparatus 20.

Services 72 of communication system 82 are adapted to communicate network variables 84 using packets. The packet structure utilized by services 72 includes, in at least one embodiment, the following four items: the sending node's device ID, the receiving node's device ID, one or more network variables 84, and a data integrity checksum token. When the arbiter node 58 holds the token, only the arbiter node 58 can transmit on the medium 60. All other nodes 58 respect this rule and do not transmit anything during this time.

At a scheduled time, the arbiter node 58 passes the token (via a serial message) to one of the other nodes 58. While the recipient node 58 holds the token, only the recipient node 58 can transmit on medium 60. Again, all other nodes 58 respect this rule and do not transmit anything during this time. When the recipient node 58 has no more data to transmit, it passes the token (via serial message) to another node 58 on the network 62 (typically returning it to the arbiter node 58). That subsequent recipient (which may be the arbiter node 58) then chooses the next node 58 in a sequence and passes the token to that node 58. This process is repeated until all nodes 58 have been given a chance to transmit on the medium 60. Table 3 illustrates an example of this process.

TABLE 3

Token Passing for Serial Networks

| Schedule Step | deviceID1 (arbiter) | device-ID3 | device-ID10 | device-ID20 |
|---|---|---|---|---|
| 0 | (token) ↘ | | | |
| 1 | | ↘ (token) ↙ (transmit netVars 84) | | |
| 2 | (token) ↘ | | | |
| 3 | | → | → (token) ↙ (transmit netVars 84) | |
| 4 | (token) ← ↘ | ← | | |
| 5 | | → | → | → (token) ↙ (transmit netVars 84) |
| 6 | (token) ← | ← | ← | ← |

If, after a prescribed timeout period, there is no token-passing activity on the bus (medium 60), the arbiter node 58 assumes that the current recipient node 58 has failed and it reclaims the token to begin scheduling passing of the token to other nodes 58 again. Table 4 below illustrates how system 82 maps to the OSI model for this type of serial network packet communication.

TABLE 4

OSI Mapping for Serial Networks

| OSI Layer | Network Components |
|---|---|
| Application | System 82 packet<br>Network variables 84 |
| Presentation | |
| Session | |
| Transport | |
| Network | System 82 packet<br>Sending node ID<br>Receiving node ID |
| DataLink | System 82 packet<br>CRC16 Checksum |
| Physical | (RS-232, RS-485, etc.) |

System 82 can also or alternatively be integrated into other types of conventional networks having network protocols that detect bus contention. With these buses, the hardware often automatically manages multiple nodes 58 communicating simultaneously or nearly simultaneously. Ethernet is an example of such a network type. When system 82 is integrated into these types of networks, there is no need to use the above-described token mechanism because such networks are designed to allow two nodes 58 to talk at the same time or substantially the same time (since the hardware ensures proper delivery). In these types of bus-contention detection networks, the components of system 82 are mapped to the OSI model in the manner illustrated in table 5 below.

TABLE 5

OSI Mapping for Bus-Contention Detection Networks

| OSI Layer | Network Components |
|---|---|
| Application | System 82 packet<br>Sending node ID<br>Receiving node ID<br>Network variables 84<br>CRC16 Checksum |
| Presentation | |
| Session | |
| Transport | |
| Network | Ethernet, etc. |
| DataLink | |
| Physical | |

System 82 can also or alternatively be integrated into other types of networks having advanced conventional network stacks. Such advanced stacks allow more advanced routing, error detection and packet delivery assurances. Examples of these types of network include networks configured to utilize the conventional Internet Protocol (IP), User Datagram Protocol (UDP), Transport Control Protocol (TCP), and/or other higher level protocols. As with the bus-contention detection networks, there is no need for system 82, when used with these types of advanced network protocols, to use the token passing communication mechanism discussed above. This is because these higher level protocols allow more than one device to communicate at the same time using network 62 (the conventional network stack ensures proper delivery). When used with these types of advanced protocols, system 82 maps to the OSI model in the manner shown below in Table 6.

TABLE 6

OSI Mapping for Networks with Advanced Protocols

| OSI Layer | Network Components |
|---|---|
| Application | System 82 packet<br>Sending node ID<br>Receiving node ID<br>Network variables 84<br>CRC16 Checksum |
| Presentation | |
| Session | |
| Transport | UDP, TCP, etc. |
| Network | IP, etc. |
| DataLink | Ethernet, etc. |
| Physical | |

Still another type of conventional network with which system 82 can work is a message-based network that delivers small chunks of information in messages, rather than relatively large packets. Such networks typically allow for more advanced routing, error detection and message delivery assurances. An example of this type of message-based network is a Controller Area Network (CAN). When network 62 is implemented as a CAN network with a CAN bus for communication medium 60, system 82 does not utilize a token based network contention mechanism because the CAN stack ensures proper deliver of simultaneously transmitted messages. However, when implemented using a CAN network, or other types of message based networks, system 82 fragments and defragments individual packets, as necessary, prior to sending them over the underlying network in order to fit the packets into the size limits of the CAN messages (or whatever other type of messages are used by the selected message based network). Table 7 below illustrates how system 82 is mapped to the OSI models when used with these types of message based networks.

TABLE 7

OSI Mapping for Message-Based Networks

| OSI Layer | Network components |
| --- | --- |
| Application | System 82 packet |
| | Sending node ID |
| | Receiving node ID |
| | Network variables 84 |
| | CRC16 Checksum |
| Presentation | |
| Session | |
| Transport | System 82 Fragmentation Layer |
| | Fragment id |
| Network | |
| DataLink | CAN Object Layer |
| | CAN Transfer Layer |
| Physical | CAN Physical Layer |

System 82 is adapted to be used on patient care devices having one or more network bridges wherein one or more subnetworks, or network portions, are not directly connected to each other. For example, in the embodiment of control system 56 shown in FIG. 2, graphics engine node 58*a* is directly coupled to both footboard node 58*b* and a plurality of other nodes 58. Footboard node 58*b*, however, is only connected directly to graphics node 58*a*. Footboard node 58*b* therefore could be treated as a separate subnetwork with graphics engine node 58*a* acting as a bridge to the rest of network 62. Alternatively, footboard node 58*b* could be coupled directly to medium 60 in a manner that bypasses graphics engine node 58*a*.

When system 82 is implemented on a network 62 having one or more bridges, the interconnection between the subnetworks or network portions carried out by the bridge often uses a single microcontroller that can connect to both networks independently. Because system 82's packet structure remains identical regardless of the underlying physical layer (and in some cases, higher layers) of network 62, it is trivial to pass system 82 information from one subnetwork to another via a simple software bridge. For example, in situations where both sides of the bridge are of the same type, the bridge simply copies the packet received from the network adapter coupled to one of the subnetworks and forwards it to the network adapter that is coupled to the other one of the subnetworks. For cases where the subnetworks on either side of the bridge are dissimilar, the bridge node 58 transforms the packets, as necessary, to accommodate the differences between the types of networks on the two sides of the bridge.

For some embodiments of control system 56, it is desirable to retain some packets within one of the subnetworks and not pass certain packets to the other subnetwork(s). Such situations may arise where only a few items of data are of interest to both subnetworks, or wherein one or more microcontrollers of some nodes 58 on a side of a bridge are not powerful enough to process all the network data coming from the other side of the bridge. In such scenarios, system 82 may be easily implemented to accommodate this by registering two identical network variables 84, one for each subnetwork, and then have the mainline software application 70 of the bridge node 58 read the value of one of the network variables 84 and write that value to the other of the identical network variables 84 in order to pass data between the subnetworks. Other manners of segmenting and/or limiting the distribution of network variables 84 among the various nodes 58 may also or additionally be used.

In some instances, it may be inconvenient or inefficient to transmit network variables 84 in separate packets. For example, it may be inefficient or undesirable to send fifty readings from a particular sensor or node by registering fifty unique network variables 84. In such cases, system 82 can be adapted to send such data using a Binary Large OBject (BLOB). A BLOB is a block of data or an arbitrary length (up to 4000 bytes long). Services 72 of system 82 are not programmed to have an understanding of what is encoded within a BLOB, but instead are programmed to know how many bytes there are to transmit and receive in a particular BLOB. Mainline applications 70 are programmed in a manner that assigns meaning to the data within the BLOBs.

In some embodiments, system 82 uses BLOBs for transmitting node parameters to other nodes 58. A node parameter is a persistent piece of stored data that is not lost after a node 58 loses power. Node parameters are stored and retrieved using a three-way voting scheme to protect against data loss. This means that a single piece of data is stored three times in persistent memory. If any two out of the three stored values match (win the vote), then that is the value system 82 uses. Thus if any one of the three stored values is somehow corrupted in memory, the node parameter is still usable.

In some situations, a diagnostic device, such as a laptop computer or the like, is coupled to network 62 and sends out requests for device parameters. The diagnostic device acts as anther node on network 62, such as node 58*j* in FIG. 4. Alternatively, or additionally, any of nodes 58*a-i* of FIG. 3 may request node parameter information from any of the other nodes 58. Such requests are carried out by formulating a special command inside a BLOB data block. A pseudocode example of such a command looks like the following: "Get NodePar 1,2,10,21,55,66 from deviceID 44". (Note that the bits and bytes of the actual message can be encoded differently, and this is for illustrative purposes only). DeviceID 44 responds with a message, such as, for example, the following pseudocode message: "Returning NodePar 1=#, 2=#, 10=#, 21=#, 55=#, 66=4 from deviceID 44".

System 82 is adapted to allow BLOBs to be used in a similar manner for setting remote node parameters. Such setting of remote node parameters may be used when a diagnostic node (e.g. node 57*j* of FIG. 4) is coupled to network 62 and executes a mainline application 70 that monitors one or more individual system characteristics of control system 56. The diagnostic node may also or additionally execute a mainline application 70 that tests aspects of system 82 by modifying individual node parameters and seeing the effect of the modified node parameters on system 82.

System 82 is also adapted to allow software on each of the nodes 58 to be upgraded or changed by using one or more BLOBs as network variables. This is done without using any specialized firmware upgrade protocol, and without needing to disable all other nodes 58 on the network 62 during the upgrade of one node 58. An external node, such a node 58*j* of FIG. 4, writes to a page of flash memory of a particular node 58 that is to be upgraded by formulating a special command inside a BLOB. A pseudocode example of such a special command is the following: "Write the following block of data to memory address 1000 on deviceID 44 (a block of data follows containing all or a portion of the upgraded software)". A similar "Read" command in the BLOB data block also exists to allow data to be retrieved from a remote node's memory. To verify the integrity of data transferred via a BLOB, a BLOB-based checksum command is also implemented, in at least some embodiments.

System 82 is adapted to keep one or more logs of events that occur with respect to network 62 and the software (services 72, applications 70, and drivers 74) running on nodes 58. Each data log entry occupies three node parameters and consists of the time, date and an event code. The full log includes multiples of these three entries (e.g. for a 10-entry log, 30 device parameters are present). For a mainline application 70 to access a data log, such as a mainline application executing on a diagnostic node, the mainline application 70 needs only to know the first node parameter of the log and the number of entries in the log.

A simple function call from a service 72 within a node 58 is made to add log entries at will. The function call automatically discards the oldest entry when the log is full and overwrites it with the newest. A remote node can read a data log from a node by formulating a special command inside a BLOB data block. A pseudocode example of such a command is as follows: "Read the data log that starts at nodePar 50 and has 2 entries from deviceID 44". An illustrative pseudocode response is: "The data log contains [2017-01-01 10:35 am Event 100], [2017-01-02 4:50 pm Event 101]".

As illustrated more clearly in FIG. 4, each node 58 executes one or more services 72 that include a plurality of reusable components, such as components 76, 78, and 80. Components 76, 78, and 80 are reusable in the sense that they do not change if different types of networks 62 are used (e.g. Ethernet, CAN, RS-485, RS-232, $I^2C$, etc.). This enables changes to the underlying network 62 of patient support apparatus 20 to be made without reprogramming these components. Further, these components can also be used in new patient support apparatuses 20 having a different underlying network 62, or incorporated into different models of patient support apparatuses that use a different underlying network 62, without being changed or reprogrammed. Alternatively, or additionally, these reusable components can be reused without change when different mainline applications 70 are installed on any of nodes 58. Similarly, when these reusable components are installed on a different model of patient support apparatus 20 that uses one or more mainline applications 70 that are different from another model of patient support apparatus 20, there is no need to change these reusable components. Instead, only the hardware driver portion 74 needs to be changed (assuming the different models of patient support apparatuses 20 uses different network hardware).

One of the many reusable functions of service 72 that is included in some embodiments of system 82 is a time management function that manages timing for the rest of system 82. This function uses multiple data structures and functions that store and manage the calendar time and date. These data are used by other functions of system 82 carried out by service 72, such as the logging functions (that include timestamp entries) and the communication functions that send and receive messages. Table 8 below illustrates examples of components of the time management function separated into reusable subcomponents and a hardware-specific driver.

TABLE 8

Time Management Components

| Subcomponent_System-82_Core | Driver_System_82_Core |
|---|---|
| System82.time_100 us | Hardware timer interrupt |
| System82.time_100 ms | ← handler for this processor |
| System82_Core_TimeExpired( ) | |
| System82_Core_TimeElapsed( ) | |
| other core functions | |

As was noted previously, although communication system 82 has been described herein as specifically for use in a patient support apparatus 20, it will be understood that it may be incorporated into other patient care devices. As one example, communication system 82 may be incorporated into a thermal control system that controls the temperature of a patient. One such suitable thermal control system is described in more detail in commonly assigned U.S. patent application Ser. No. 14/282,383 filed May 20, 2014, by inventors Christopher Hopper et al., and entitled THERMAL CONTROL SYSTEM, the complete disclosure of which is incorporated herein by reference. Other types of thermal control systems, as well as other types of patient care devices, may also incorporate the communication system 82 described herein.

Various additional alterations and changes can be made to the above-described embodiments without departing from the spirit and broader aspects of the disclosure as defined in the appended claims, which are to be interpreted in accordance with the principles of patent law including the doctrine of equivalents. This disclosure is presented for illustrative purposes and should not be interpreted as an exhaustive description of all embodiments of the disclosure or to limit the scope of the claims to the specific elements illustrated or described in connection with these embodiments. For example, and without limitation, any individual element(s) of the described disclosure may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present disclosure is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A patient support apparatus comprising:
a support surface adapted to support a person;
a plurality of force sensors adapted to detect a weight of the person when the person is supported on the support surface;
a first node having a first controller in communication with the plurality of force sensors, the first node adapted to execute a first software program and a first service, the first software program adapted to read values from the plurality of force sensors in response to a user activating a control to take a weight reading of the person, the first software program further adapted to assign the values to first private variables, the first service adapted to copy the first private variables into first public variables and to broadcast the first public variables over a communication medium; and
a second node having a second controller adapted to execute a second service, the second service adapted to receive the first public variables from the first node via the communication medium and to copy the first public variables into second private variables, the second controller further adapted to execute a second software program that reads the second private variables but not the first public variables, the second software program further adapted to send the second private variables offboard the patient support apparatus to a local area network.

2. The patient support apparatus of claim 1 wherein the second controller interrupts execution of the second software program to copy the first public variables into second private variables.

3. The patient support apparatus of claim 1 wherein the second software program does not include instructions for retrieving the first public variables from the first node.

4. The patient support apparatus of claim 1 wherein the first software program is further adapted to automatically assign updated values from the force sensors to the first private variables, and the first service is further adapted to automatically copy the first updated private variables into first updated public variables and to broadcast the first updated public variables over the communication medium.

5. The patient support apparatus of claim 1 further including a third node having a third controller, the third controller adapted to receive the first public variables from the first controller via the communication medium, and the third controller further adapted to copy the first public variables into third private variables and to execute a third software program that reads the third private variables but not the first public variables.

6. A patient support apparatus comprising:
a support surface adapted to support a person;
a first node having a first controller, the first controller adapted to execute a first software program that is adapted to capture sensor readings from a first sensor onboard the patient support apparatus, the first software program further adapted to set a first private variable equal to a first value;
a first service executed by the first controller and adapted to set a first public variable equal to the first value and to transmit the first public variable over a communication medium;
a second node having a second controller adapted to receive the first public variable from the first node via the communication medium, check to see if the first public variable is registered at the second node, and if the first public variable is registered, use the first value of the first public variable in carrying out at least one function, the second node further adapted to take sensor readings from a second sensor onboard the patient support apparatus; and
wherein the first public variable defines a synchronization time at which the first node is adapted to capture a first sensor reading from the first sensor at the same time as the second node captures a second sensor reading from the second sensor.

7. The patient support apparatus of claim 6 wherein the first software program does not include instructions for transmitting the first public variable over the communication medium.

8. The patient support apparatus of claim 6 wherein the second node includes a second software program and a second service, and the second service checks to see if the first public variable is registered at the second node.

9. The patient support apparatus of claim 8 wherein the second service is adapted to set a second private variable equal to the first value of the first public variable if the first public variable is registered at the second node.

10. The patient support apparatus of claim 9 wherein the second software program reads the second private variable but not the first public variable.

11. The patient support apparatus of claim 8 wherein the first and second software programs are independent of a data link layer and a physical layer of a communications protocol used to transmit the first public variable over the communication medium.

12. The patient support apparatus of claim 6 wherein the patient support apparatus further comprises a plurality of siderails, a lift system adapted to raise and lower the support surface, and a plurality of wheels adapted to allow the patient support apparatus to be wheeled to different locations.

* * * * *